(12) United States Patent
Sugita et al.

(10) Patent No.: US 7,780,598 B2
(45) Date of Patent: Aug. 24, 2010

(54) SONODYNAMIC TREATMENT APPARATUS AND METHOD OF CONTROLLING THE SAME

(75) Inventors: Nami Sugita, Hiki (JP); Ken-ichi Kawabata, Kodaira (JP); Takashi Azuma, Kawasaki (JP); Shin-ichiro Umemura, Muko (JP)

(73) Assignee: Hitachi, Ltd., Tokyo (JP)

( * ) Notice: Subject to any disclaimer, the term of this patent is extended or adjusted under 35 U.S.C. 154(b) by 899 days.

(21) Appl. No.: 11/476,866

(22) Filed: Jun. 29, 2006

(65) Prior Publication Data

US 2007/0038099 A1    Feb. 15, 2007

(30) Foreign Application Priority Data

Jul. 1, 2005    (JP)    ............................. 2005-194238

(51) Int. Cl.
*A61B 8/00*    (2006.01)
(52) U.S. Cl. .......................................... 600/439; 601/2
(58) Field of Classification Search ................. 600/439; 601/2
See application file for complete search history.

(56) References Cited

U.S. PATENT DOCUMENTS

| | | | |
|---|---|---|---|
| 4,610,255 A | | 9/1986 | Shimura et al. |
| 5,520,188 A | * | 5/1996 | Hennige et al. ............. 600/459 |
| 5,523,058 A | * | 6/1996 | Umemura et al. ........... 422/128 |
| 5,694,936 A | * | 12/1997 | Fujimoto et al. ............ 600/439 |
| 6,113,558 A | * | 9/2000 | Rosenschein et al. .......... 601/2 |

FOREIGN PATENT DOCUMENTS

JP    2000-229098    1/1999

OTHER PUBLICATIONS

Office Action from the Japanese Patent Office, in Japanese, dated May 15, 2009.
International Search Report for PCT/JP 97/02285 dated Sep. 24, 1997.

* cited by examiner

*Primary Examiner*—Long V Le
*Assistant Examiner*—Saurel J Selkin
(74) *Attorney, Agent, or Firm*—Stites & Harbison, PLLC; Juan Carlos A. Marquez, Esq.

(57) ABSTRACT

In a sonodynamic treatment apparatus including: a first ultrasound radiating unit for radiating diagnostic ultrasound; a second ultrasound radiating unit for radiating treatment ultrasound; an echo detection unit for detecting an ultrasound echo; a diagnostic controller for radiating the diagnostic ultrasound with the first ultrasound radiating unit and detecting the ultrasound echo corresponding the diagnostic ultrasound; an echographic controller for processing an echographic image on the basis of the detected ultrasound echo; and a treatment controller for radiating the treatment ultrasound with the second ultrasound radiating unit, radiation of the treatment ultrasound with the second ultrasound radiating unit is controlled to have a predetermined exposure duration and a predetermined pause duration of the treatment ultrasound, and the echographic image is generated on the basis of the ultrasound echo during the pause duration of the treatment ultrasound exposure with the diagnostic image generator. The treatment ultrasound may be weakened after detection of a bubble generated by the treatment ultrasound.

15 Claims, 11 Drawing Sheets

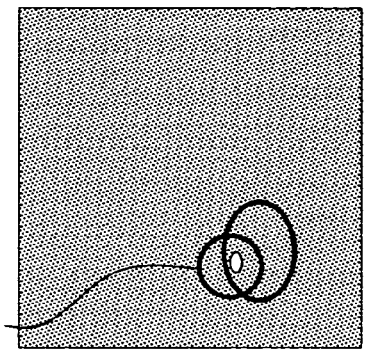
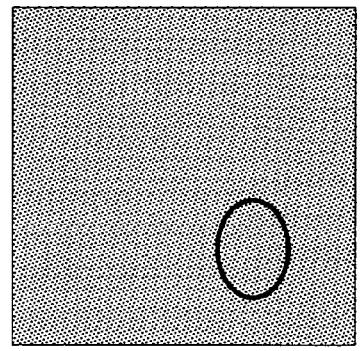
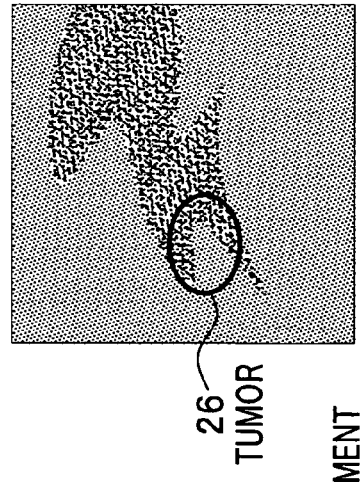

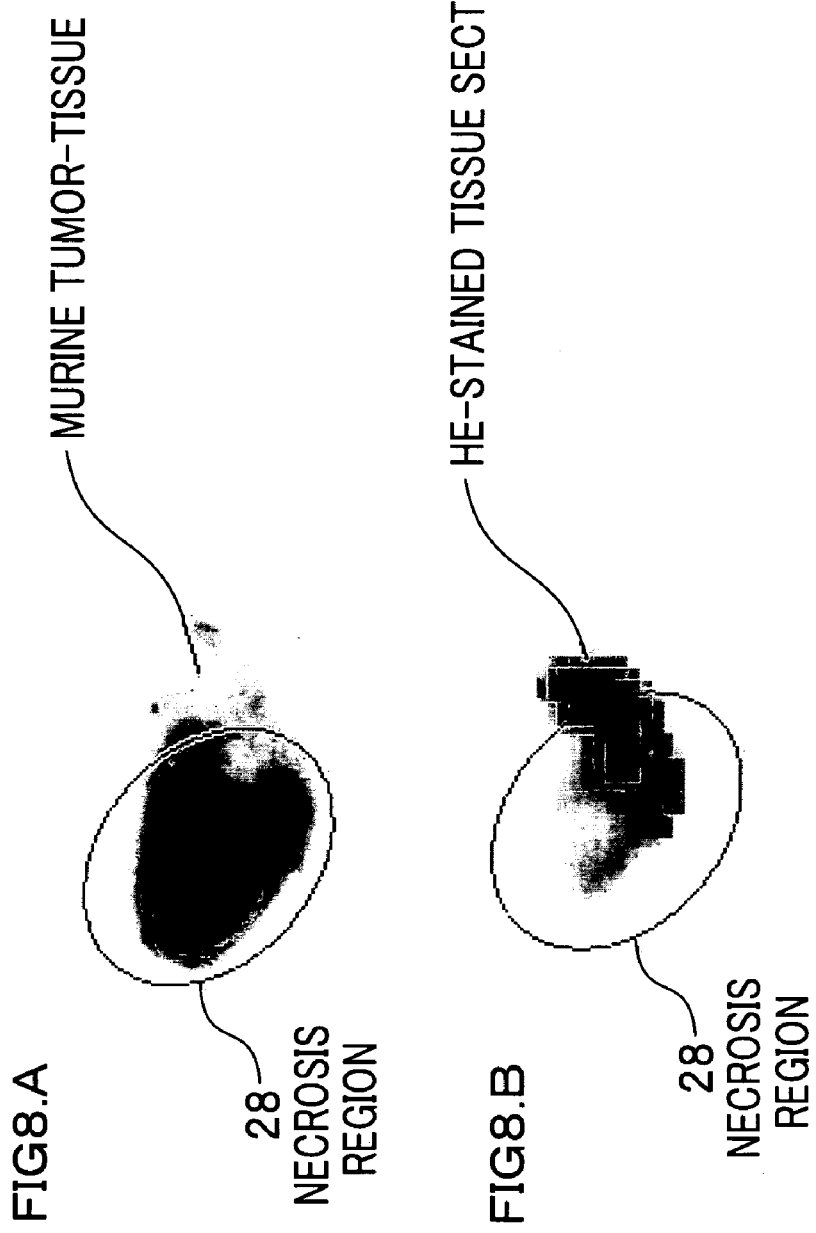

FIG.9

| BRIGHTNESS CHANGE | WITH DAMAGE IN TISSUE | WITHOUT DAMAGE IN TISSUE |
|---|---|---|
| WITH | 3 | 0 |
| WITHOUT | 1 | 2 |

FIG.11

| BRIGHTNESS CHANGE | WITH DAMAGE IN TISSUE | WITHOUT DAMAGE IN TISSUE |
|---|---|---|
| WITH | 5 | 0 |
| WITHOUT | 1 | 2 |

SONODYNAMIC TREATMENT APPARATUS AND METHOD OF CONTROLLING THE SAME

CROSS REFERENCE TO RELATED APPLICATIONS

The present application is based on Japanese application JP 2005-194238, filed on Jul. 1, 2005, the content of which is hereby incorporated by reference into this application.

BACKGROUND OF THE INVENTION

1. Field of the Invention

The present invention relates to a sonodynamic treatment apparatus for sonodynamic treatment using an ultrasound and a method of controlling monitoring the same, and particularly to a sonodynamic treatment apparatus for performing the sonodynamic treatment using the ultrasound together with a medicine for the sonodynamic treatment activated by cavitation generated by the ultrasound radiation and a method of monitoring the same.

2. Description of the Related Art

Ultrasound scanners are widely used as apparatuses utilizing ultrasounds in a medical technical field. The ultrasound scanners are superior in real time among various types of diagnostic imaging apparatuses currently in use and have advantageous effects such as low costs and small sizes.

Further, the ultrasound is utilized in treatment for cancer in addition to diagnosis. As a medical treatment method using the ultrasound, is disclosed High Intensity Focused Ultrasound (HIFU) of a thermal coagulation treatment in which a tissue is coagulated to go necrosis by energy of the ultrasound which is absorbed by the tissue and converted into heat (see, for example, P. P. Lele, "Ultrasound; medical applications, biological effects and hazard potential", Plenum Press New York 1987:275-306.) Such the thermal coagulation treatment begins to be actually used for patients of benign prostatic hyperplasia, prostatic cancer, breast cancer, and the like.

As described above, the ultrasound, capable of being used both for the diagnosis and the treatment, provides an integration system which is efficient and effective for treating patients (see, for example, WO96/506636.)

However, the thermal coagulation treatment, radiating a focused ultrasound having an acoustic intensity more than 1 kW/cm$^2$ toward an affected part, has a possibility of an increased risk of a patient if an aiming point is off an affected part. Further, the thermal coagulation treatment is considered to be unsuitable for treating invasive and disseminated cancer in which normal tissues and cancer tissues are complicated.

On the other hand, a sonodynamic treatment using an ultrasound having a low acoustic intensity from several watts/cm$^2$ to several tens watts/cm$^2$ is disclosed (see, for example, Yumita et al., March 1989, Jpn. J. Cancer Res., 80: 219-222.) The sonodynamic treatment is a method for treating a patient by activating a medicine for the sonodynamic treatment previously administered in the patient using a phenomenon called cavitation generated by ultrasound insonation.

The cavitation is a sequential phenomenon in which a bubble is generated by the ultrasound insonation, the generated bubble grows gradually, and the grown bubble collapses suddenly. The collapse of the bubble at a last process of the cavitation generates an extremely high pressure (hundreds of atmospheric pressures) and an extremely high temperature (thousands degrees) in very short time with formation of a unique reaction field around the bubble.

Among medicines for the sonodynamic treatment, is disclosed a medicine accumulating in a tumor to decrease a threshold for a level of ultrasound necessary for the cavitation, such as rose bengal derivative, upon being located in the reaction field generated by the cavitation, showing an antitumor effect (see, for example, a pamphlet of WO98/01131.)

As mentioned above, the sonodynamic treatment is expected to have a high selectivity because the affected part is double targeted with the medicine and the ultrasound.

Further, for the sonodynamic treatment, are disclosed methods of radiating an ultrasound having a lower acoustic intensity enough to cause the cavitation than conventional one. For example, Japanese laid open patent application publication No. 2-126848 discloses a method of radiating the ultrasound in which acoustic fields are switched. A pamphlet of WO94/06380 discloses a method of superimposing a second harmonic on the fundamental. It is also disclosed that a method of periodic shifting of second-harmonic phase on the fundamental (see, for example, Kawabata et al., (2003) Jpn. J. Appl. Phys., 42: 3246-3250.)

Both methods efficiently grow the cavitation by promoting growth of the bubble generated by ultrasound exposure up to a size resonant with the frequency of the radiated ultrasound.

In addition, for example, it is disclosed that the growth of the bubble once generated requires to be successively exposed to three or more pulses of the ultrasound (see, for example, Xu et al. (2003) IEEE Ultrasonics Symposium Proc., 1086-1089 and Xu et al. (2004) IEEE Trans. Ultrason., Ferroelect. Freq. Contr., 51: 726-736.)

A plurality of methods are disclosed for monitoring a treatment area during Lithotripsy and ultrasound thermal coagulation treatment. For example, Japanese Patent No. 2644217 discloses a method of confirming a position of a calculus using a weak ultrasound before treatment. Japanese Patent No. 3225526 discloses a method of confirming a position of a broken calculus and a position of collapsed cavitation by detecting positions of even-number-times harmonics on images of the ultrasound in a plurality of different directions. Japanese laid open patent application publication No. 2003-33365 discloses a method of confirming that a temperature reaches such a value as to surely cause thermal denaturation in a tissue by confirming generation of a bubble by detecting even-number-times harmonics.

Particularly, it is disclosed that a method of making observation possible under treatment at a treatment area by stopping radiation of the ultrasound for treatment only when an ultrasound for diagnosis is used for visualizing an area around the treatment area by synchronizing an ultrasound diagnosis apparatus with a thermal coagulation treating apparatus to overcome a difficulty in ultrasound diagnosis due to interference of the ultrasound for the thermal coagulation under radiation with ultrasound for diagnosis (see, for example, Vaezy et al. (2000) Ultraso. Med. Biol., 27: 33-42.)

Further, in the thermal coagulation treatment, are disclosed technologies in which operation of the ultrasound is made to acquire an ultrasound diagnosis image only while radiation of the ultrasound for treatment is stopped (see, for example, U.S. Pat. No. 6,095,980 and Japanese laid open patent application publication No. 2000-229098.)

As mentioned above, the sonodynamic treatment is expected as an effective treatment method for a tumor because it provides a little potential risk to a patient. Further, in the sonodynamic treatment, a method of the ultrasound exposure which efficiently causes a cavitation phenomenon as a source of treatment using an ultrasound of which acoustic intensity is relatively low in the sonodynamic treatment.

SUMMARY OF THE INVENTION

An aspect of the present invention provides a sonodynamic treatment apparatus comprising: a first ultrasound radiating unit for radiating a diagnostic ultrasound; a second ultrasound radiating unit for radiating a treatment ultrasound; an echo detection unit for detecting an ultrasound echo; a diagnostic controller for radiating the diagnostic ultrasound with the first ultrasound radiating unit and detecting the ultrasound echo corresponding the diagnostic ultrasound; an echographic controller for processing an echographic image on the basis of the detected ultrasound echo; and a treatment controller for radiating the treatment ultrasound with the second ultrasound radiating unit, wherein the treatment controller comprises a pulse generator for controlling the treatment ultrasound exposure with the second ultrasound radiating unit to have a predetermined exposure duration and a predetermined pause duration of the treatment ultrasound and the diagnostic image processor processes the echographic image on the basis of the ultrasound echo during the pause duration, for the treatment ultrasound exposure.

BRIEF DESCRIPTION OF THE DRAWINGS

The object and features of the present invention will become more readily apparent from the following detailed description taken in conjunction with the accompanying drawings in which:

FIGS. 7A to 7D are illustrations of echographic images displayed on a display in the example 1;

FIG. 8A is an illustration of a murine tumor-tissue section after treatment according to the present invention without staining;

FIG. 8B is an illustration of murine tumor-tissue sections after treatment according to the present invention and HE-staining;

FIG. 9 illustrates a table showing a correlation between a group observed a brightness change on the echographic image during the treatment and a group observed a treatment effect on the murine tumor-tissue sections according to the present invention;

FIG. 11 illustrates a table showing a correlation between a group observed the brightness change on the echographic image during the treatment and a group observed a treatment effect on the murine tumor-tissue sections in the example 2.

The same or corresponding elements or parts are designated with like references throughout the drawings.

DETAILED DESCRIPTION OF THE INVENTION

Prior to describing an embodiment of the present invention, the above-mentioned related art will be further argued.

In the above-mentioned related art, there is a problem of difficulty in providing a high reproducibility to cause the cavitation phenomenon.

In addition, in the related art because an appropriate echographic image cannot be displayed during ultrasound exposure for the treatment, a treatment effect cannot be judged until it is actually confirmed that the tumor is denatured after several days passed from the ultrasound exposure.

The inventors provide a sonodynamic treatment apparatus capable of treatment with monitoring generation of a bubble by the cavitation effective for the sonodynamic treatment.

Hereinafter, with reference to drawings will be described the embodiment in details.

Figure 1:
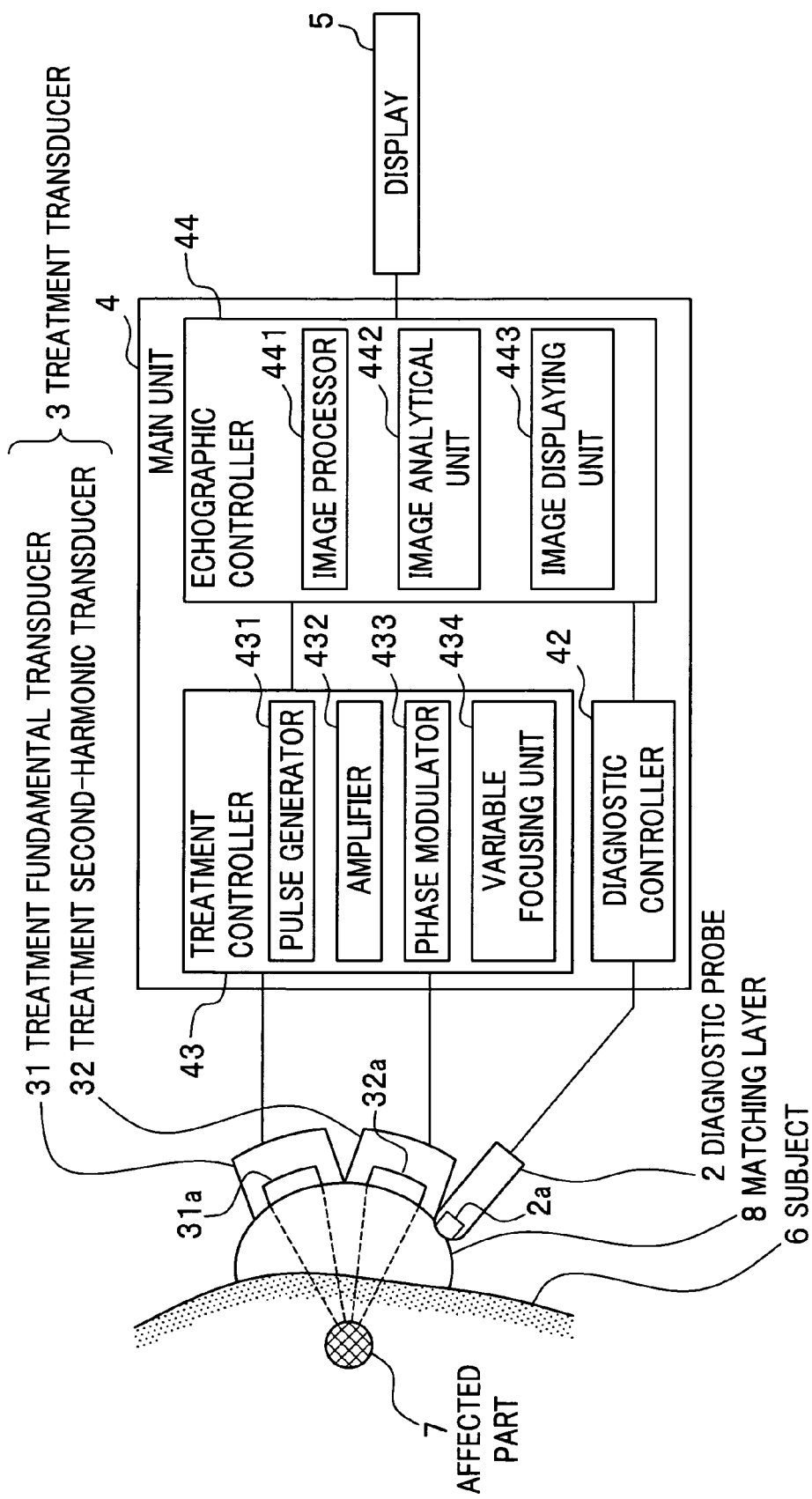
FIG. 1 is a block diagram of a sonodynamic treatment apparatus according to an embodiment of the present invention.

FIG. 1 is a block diagram of a sonodynamic treatment apparatus according to the embodiment of the present invention. As shown in FIG. 1, the sonodynamic treatment apparatus 1 includes a diagnostic probe 2, a treatment transducer 3, a main unit 4, and a display 5.

A subject 6 including an affected part 7 is administered a predetermined medicine for sonodynamic treatment (hereinafter referred to as a sonodynamic sensitizer). A composition of the sonodynamic sensitizer is not limited to this if the sonodynamic sensitizer is any activated by action of cavitation generated when the affected part 7 exposes to a treatment ultrasound. However, preferably, the sonodynamic sensitizer has such a property as to be selectively located at the affected part 7 requiring treatment and such a property that a threshold of the ultrasound necessary for generating the cavitation is lowered.

Here, the term "subject" means a target to be treated by the sonodynamic treatment apparatus 1 of the embodiment. However, it may be any as long as the cavitation may occur inside thereof. For example, the subject 6 may be an animal or a plant, a living tissue of an animal or a plant, a suspension stored in a container, and the like.

<Diagnostic Probe>

The diagnostic probe 2 is provided to radiate diagnostic ultrasound pulses toward the affected part 7 of the subject 6 and receive an ultrasound echo corresponding to the diagnostic ultrasound pulses to diagnose the subject 6.

The diagnostic probe 2 is configured to include an oscillator 2a for converting an electric signal into oscillation and converting the oscillation into an electric signal. For the oscillator 2a may be used, for example, a magnetostriction resonator, and a piezoelectric element. Further, preferably, a plurality of oscillators 2a may be arranged to diagnose a predetermined region of the subject 6 to provide on the display 5 a plurality of scanning lines corresponding to the oscillators 2a, respectively. In addition, preferably, the oscillator 2a is arranged on a plane surface or a convex surface to diagnose a broader range.

Further, the diagnoses probe 2 is connected to the main unit 4.

<Treatment Transducer>

The treatment transducer 3 is provided to radiate treatment ultrasound pulses toward the affected part 7 of the subject 6 to treat the subject 6 and configured to include a treatment fundamental transducer 31 for radiating a fundamental and a treatment second-harmonic transducer 32 for radiating a second harmonic having a frequency which is twice the fundamental. The treatment fundamental transducer 31 and the treatment second-harmonic transducer 32 can be configured as the above-mentioned diagnostic probe 2 is configured. The oscillators 31a and 32a are, preferably, formed on a planer surface and a concave surface to focus the ultrasound (if only one oscillator is provided, it is formed on a plane surface or a concave surface). For example, the oscillators 31a and 32a are arranged on a partial spherical surface having an F number of one with a diameter of 6 cm to become same geometric focuses each other.

The configuration as mentioned above enables the treatment transducer 3 to easily perform superimposing between the fundamental and the second harmonic at the affected part 7 to efficiently generate the bubble. The treatment fundamental transducer 31 and the treatment second-harmonic transducer 32 are electrically connected to the main unit 4.

Further, the diagnostic probe 2, the treatment fundamental transducer 31, and the treatment second-harmonic transducer 32 are arranged to the subject 6 through a matching layer 8 including a material having a low attenuation factor to the ultrasounds (for example, degassed water) to have an increased sensitivity.

The diagnostic probe 2, the treatment fundamental transducer 31, and the treatment second-harmonic transducer 32 may be mechanically connected with each other with a holder (not shown) including a position detector (not shown) measurable of a direction of an ultrasound-radiated plane and a rotating mechanism (not shown). This configuration facilitates positioning the treatment transducer 3.

<Main Unit>

The main unit 4 performs: a process for an electronic signal corresponding to the ultrasound echo collected from the subject 6 (hereinafter referred to as "echo signal"); control regarding ultrasound transmission and reception; and control regarding generation, displaying, and analysis of an echographic image.

The main unit 4 includes a diagnostic controller 42, a treatment controller 43, and an echographic controller 44.

Parts, designated with the references 42 to 44, in the main unit 4 are provided using hardware including a CPU (Central Processing Unit) (not shown), memories (not shown) such as a ROM (Read Only Memory) (not shown), a RAM (Random Access Memory) (not shown), and a hard disk drive (not shown). The parts, designated with the references 42 to 44, in the main unit 4 correspond to programs and/or data stored in the memories or the hard disk drive. The CPU reads out the program from the memories to execute it to provide a process in each of the parts designated with the references 42 to 44.

The parts, designated with the reference 42 and 43, are configured to further include circuits (not shown) for controlling the ultrasounds transmitted and received.

<Diagnostic Controller>

The diagnostic controller 42 is electrically connected to the diagnostic probe 2 to control transmission and reception of the diagnostic ultrasound.

The diagnostic controller 42 is configured to radiate through the diagnostic probe 2 an ultrasound having a frequency of from 3 to 10 MHz and an acoustic intensity equal to or smaller than about 1 W/cm$^2$ which is usable in general ultrasound diagnostic apparatuses and receive through the diagnostic probe 2 the ultrasound echo.

Preferably, the diagnostic controller 42 is configured on the basis of an imaging method capable of extracting harmonics by comparing obtained signals by a method of radiating different ultrasounds and enhancing the harmonics to selectively detect generation of a bubble relating to the cavitation.

Will be described a process of control regarding the transmission and reception of the diagnostic ultrasound in a case that the diagnostic controller 42 is configured on the basis of the above-described imagining method.

The diagnostic controller 42 generates an electric signal (also referred to as fundamental signal) including a predetermined fundamental so as to correspond to the diagnostic ultrasound pulse as well as amplifies the echo signal from the diagnostic probe 2 with an amplification circuits (not shown) to output the amplified echo signal to an image processor 441.

Further, the diagnostic controller 42 generates a pulse signal having an opposite phase with the fundamental signal for each scanning line (also referred to as opposite phase signal) to output it to the image processor 441.

<Echographic Controller>

The echographic controller 44 generates a diagnostic image having harmonics enhanced by the echo signal and the opposite phase signal inputted from the diagnostic controller 42 to perform an analysis process.

The echographic controller 44 is configured to include an image processor 441 for generating the diagnostic image, an image analytical unit 442 for analyzing the generated diagnostic image, and an image displaying unit 443 for displaying the echographic image on the display 5.

Will be described an example of a process of generating the echographic image on the basis of the received echo signal and the opposite phase signal.

The image processor 441 samples the received echo signal and the opposite phase signal at a suitable sampling frequency to signal processing and converts the received echo signal and the opposite phase signal into digital signals with A/D converting circuits (not shown).

The image processor 441 performs a superimposing process for digital signals corresponding to the echo signal and the opposite phase signal, respectively. Out of the fundamental and the harmonics (non-linear component) included in the echo signal the fundamental is cancelled with the opposite phase signal, so that the harmonics are extracted as a margin. The harmonics tend to occur when a component showing a large change in volume in the subject 6 is included. Thus, such the imaging method capable of enhancing the harmonics is more preferable to detect the bubble in the subject 6 than a B-mode generally used in ultrasound diagnoses.

Generally, the harmonics includes those having frequencies of n times the fundamental frequency and subharmonics having frequencies of n/m times the fundamental frequency (n and m are given natural numbers). In the embodiment, although the frequencies are not specially limited as long as the bubble regarding the cavitation can be detected with the harmonics, the bubble can be detected more clearly if the echographic image is generated on the basis of the frequencies that are n ($1 \leq n \leq 3$) times $\frac{1}{3}$, $\frac{1}{2}$, and 1 of the fundamental.

The image processor 441 performs the process of generating the echographic image from the harmonics. The process of generating the echographic image can be provided by an apparatus having a configuration known in the technical field of the ultrasound diagnosis.

The image processor 441 may have a process for further enhancing the harmonics through frequency-analysis, such as fast Fourier transform and/or combining a plurality of signals of which amplitude and code are optionally changed.

The image processor 441 outputs the generated echographic image to the image displaying unit 443 to display it on the display 5 as well as outputs it to the image analytical unit 442.

The image analytical unit 442 detects the bubble regarding the cavitation from the echographic image generated by the image processor 441.

For example, the image analytical unit 442 performs a process of comparing the echographic images before and after the treatment ultrasound is radiated through the treatment transducer 3 and, when a ratio in brightness exceeds a predetermined ratio, judging that a corresponding region is one where the bubble occurs.

Information of the bubble detected by the image analytical unit 442 is outputted to the treatment controller 43.

The image analytical unit 442 may have a configuration to perform a process of storing in a database (not shown) the information of the ultrasound when the bubble occurs and disappears with relation to the data including a type of the sonodynamic sensitizer and data of the subject 6.

<Treatment Controller>

The treatment controller 43, electrically connected to the treatment fundamental transducer 31 and the treatment second-harmonic transducer 32, performs control regarding the treatment ultrasound exposure.

The treatment controller 43 is configured to radiate the ultrasound having a frequency of from about 0.5 to 4.5 MHz and an acoustic intensity equal to or less than 300 W/cm$^2$ which are used in general ultrasound treatment apparatuses through the treatment fundamental transducer 31 and the treatment second-harmonic transducer 32.

Thus, the treatment controller 43 can radiate ultrasounds having frequencies and acoustic intensities necessary for generating the cavitation in the subject 6.

More specifically, the treatment controller 43 includes a pulse generator 431, an amplifier 432, a phase modulator 433, and a variable focusing unit 434.

The pulse generator 431 generates a pulse signal defining an exposure duration, a pause duration, and stop timing of the treatment ultrasound. The exposure duration of the ultrasound is obtained by multiplying a duration of one pulse by the number of pulses. For example, the pulse generator 431 can be provided using a wave generator.

The pulse generator 431 generates the pulse signal within a total of duration necessary for generating the pulses of which the number is sufficient to generate a new bubble and grow the bubble once generated and the pause duration within a duration for which the bubble once generated does not disappear.

It is preferable that the number of the pulses necessary for growing the bubbles is greater than that of the diagnostic ultrasound used in the general ultrasound diagnostic apparatus.

Further, it is more preferable that the number of the pulses is equal to or more than three because it is disclosed that growing bubbles once generated requires to be successively exposure to more than two pulses of ultrasound in Xu et al. (2003) IEEE Ultrasonics Symposium Proc., 1086-1089 and Xu et al. (2004) IEEE Trans. Ultrason., Ferroelect. Freq. Contr., 51: 726-736.

In addition, the inventors demonstrate that the growth of the bubble is successively maintained if the pause duration is extended up to 500 ms. Here, a lower limit of the pause duration is not specially limited so far as the duration capable of generating a suitable echographic image.

Further the pulse generator 431 determines the stop timing of the ultrasound exposure on the basis of the information of the bubble inputted from the image analytical unit 442. More specifically, when information indicating that the bubble is detected is inputted from the image analytical unit 442, the pulse generator 431 starts a timer (not shown) and performs a process of stopping generating the pulse signal after a predetermined interval has passed since the information indicating the detection of the bubble is inputted. For example, performing the stop process after one minute has passed after the detection of the bubble can provide a sufficient treatment effect without an excessive exposure of the treatment ultrasound.

The pulse signal generated by the pulse generator 431 is outputted to the amplifier 432. The amplifier 432 amplifies a voltage of the pulse signal at a given gain. For example, the amplifier 432 includes an amplifying circuit.

The amplifier 432 amplifies the pulse signal not only at a fixed gain but a gain variable in time base. More specifically, the acoustic intensity of the ultrasound radiated by the treatment transducer 3 can be controlled by the amplifier 432.

The inventors demonstrate that a less amount of energy is necessary for growing once generated bubble than that necessary for generating a new bubble. In addition, the inventors demonstrate that one of steps of the cavitation can be eliminated by making a minute bubble residue as the result of collapse of the bubble a nucleus for a new bubble, so that a threshold of the acoustic intensity of the ultrasound necessary for continuously generating and growing the bubbles can be decreased.

As mentioned above, because the energy necessary for generating the bubbles regarding the cavitation can be decreased, an amount of the ultrasound radiated to the subject 6 can be decreased with the result that the risk on the subject 6 is reduced.

In consideration of this, in the embodiment, the amplifier 432 is configured to perform such control that the acoustic intensity of the treatment ultrasound is decreased when the information indicating that the bubble is detected is inputted from the image analytical unit 442.

Making the predetermined acoustic intensity of the treatment ultrasound radiated after the growth of the bubbles lower than that before the growth of the bubble can maintain the growth of once generated bubble and the generation of new bubbles with reduced risk on the subject 6. To further decrease the risk on the subject 6 it is preferable that the acoustic intensity is decreased down to a range equal to or greater than $\frac{1}{20}$ thereof and equal to or smaller than $\frac{1}{10}$ thereof. If the acoustic intensity is further lowered, because there may be a case that the growth of the bubble cannot be maintained, it is preferable to suitably determine the acoustic intensity with observation of the brightness change in the echographic image as needed.

The pulse signal amplified by the amplifier 432 is outputted to the treatment transducer 3.

The phase modulator 433 can control a phase shift between the fundamental and the second harmonic radiated through the treatment fundamental transducer 31 and the treatment second-harmonic transducer 32. In addition the phase shift can be changed with time. This configuration can suitably perform superimposing between the ultrasounds radiated by the treatment transducer 3 at the affected part in the subject 6. For example, the inventors experimentally demonstrate that making the phase shift between the fundamental and the second harmonic more than 10 ms efficiently causes the cavitation. The variable focusing unit 434 changes a focal point of the focused ultrasound.

<<Control Method by Sonodynamic Treatment Apparatus>>

Figure 2:
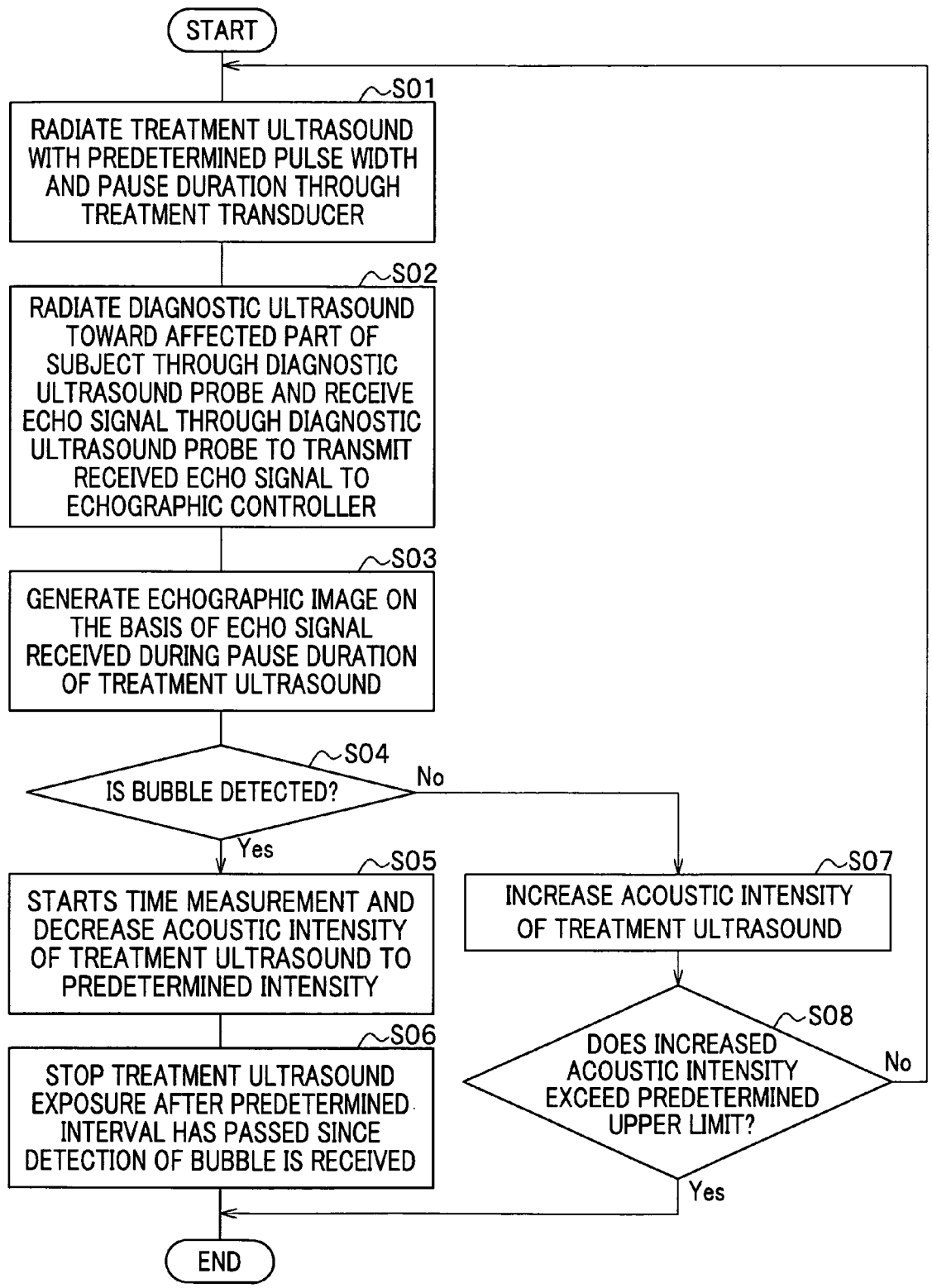
FIG. 2 depicts a flowchart illustrating a method of controlling the sonodynamic treatment apparatus to perform treatment.

Hereinafter, will be described with reference a flowchart shown in FIG. 2 a control method by the sonodynamic treatment apparatus in a case that the subject 6 is treated.

It is assumed that an operator has acquired the echographic image of the affected part with the diagnostic probe 2 and set the focus point of the treatment ultrasound radiated by the treatment fundamental transducer 31 and the treatment second-harmonic transducer 32 at a treatment position of the affected part 7.

First, the treatment controller 43 of the sonodynamic treatment apparatus 1 radiates, in a step S01, the treatment ultrasound with a predetermined pulse width (a predetermined number of pulses) and the pause duration through the treatment transducer 3.

Here, the number of the pulses and the pause duration are determined within the range in which the growth of the bubble is maintained.

Preferably, the fundamental having a predetermined frequency and the second harmonic having a frequency twice the predetermined frequency are radiated through the treatment fundamental transducer 31 and the treatment second-harmonic transducer 32 to perform superimposing of them at the affected part 7 as the treatment ultrasound.

The diagnostic controller 42 of the sonodynamic treatment apparatus 1 radiates, in a step S02, the diagnostic ultrasound at the affected part 7 of the subject 6 through the diagnostic probe 2 and receives the echo signal through the diagnostic probe 2 to transmit the received echo signal to the echographic controller 44.

The echographic controller 44 of the sonodynamic treatment apparatus 1 generates, in a step S03, the echographic image with the image processor 441 on the basis of the echo signal received during the pause duration of the treatment ultrasound.

The image analytical unit 442 of the sonodynamic treatment apparatus 1 judges, in a step S04, whether the bubble is detected. If the image analytical unit 442 of the sonodynamic treatment apparatus 1 detects the bubble (Yes, in the step S04), detection information of the bubble is transmitted to the treatment controller 43.

When receiving the detection information of the bubble, the treatment controller 43 of the sonodynamic treatment apparatus 1 starts, in a step S05, time measurement as well as performs control for decreasing an acoustic intensity of the treatment ultrasound to a predetermined intensity.

After a predetermined interval is passed since the detection of the bubble is received, the treatment controller 43 of the sonodynamic treatment apparatus 1 performs, in a step S06, control of stopping the treatment ultrasound exposure.

If detecting no bubble (No, in the step S04), the image analytical unit 442 of the sonodynamic treatment apparatus 1 transmits information of no detection of the bubble to the treatment controller 43.

The treatment controller 43 of the sonodynamic treatment apparatus 1 performs, in a step S07, control for increasing the acoustic intensity of the treatment ultrasound.

The treatment controller 43 of the sonodynamic treatment apparatus 1 judges, in a step S08, whether the increased acoustic intensity exceeds a predetermined upper limit. If the increased acoustic intensity does not exceed the predetermined upper limit (No, in the step S08), processing returns to the step S01.

If the increased acoustic intensity exceeds the predetermined upper limit (Yes, in the step S08), the processing is finished with assumption that the bubble cannot be generated.

As described above, the sonodynamic treatment apparatus 1 according to the embodiment can radiate the ultrasound, wherein the acoustic intensity of the treatment ultrasound radiated during the sonodynamic treatment can be suppressed to a minimally necessary value to decrease the risk on the subject 6.

The present invention is not limited to the above-described embodiment.

More specifically, the diagnostic controller 42 is not limited to a configuration using the above-described imaging method as far as it can detect the bubble. For example, the diagnostic controller 42 may be configured on the basis of a known pulse inversion-mode or a second-harmonic method.

Further, radiation of the ultrasound from the treatment transducer 3 may synchronize with the transmission and reception of the echo signal through the diagnostic probe 2. In this case, for example, it is possible to adopt such a pulse sequence that the diagnostic and treatment ultrasounds are alternately radiated through the diagnostic probe 2 and the treatment transducer 3. Then, the image processor 441 generates the echographic image on the basis of the echo signal received through the diagnostic probe 2.

In the embodiment, superimposing between the echo signal and the opposite phase signal to extract the harmonics is performed after they are converted into digital signals. However, superimposing may be performed in any of steps of the ultrasound and analog electric signals.

In the embodiment, to monitor the brightness change on the diagnostic image, the acoustic intensity of the treatment ultrasound is increased, and if the brightness change is not detected although the acoustic intensity is increased to the predetermined upper limit, the process is finished. However, it is also possible to detect the brightness change by further increasing the frequency of the treatment ultrasound. For example, in the sonodynamic treatment apparatus 1 according to the embodiment, the frequency of the treatment ultrasound can be increased up to 4.5 MHz.

Further, if the frequency of the treatment ultrasound exceeds 2 MHz, treatment ultrasound exposure may be controlled to have an extremely short exposure duration with increase of the treatment ultrasound to a predetermined acoustic intensity. This control is applicable to a case that the sonodynamic treatment being performed with the sonodynamic treatment apparatus 1 according to the embodiment is switched to the thermal coagulation treatment.

<Modification of Treatment Transducer>

In the above-mentioned embodiment, the oscillators 31a and 32a having concave shape to focus the ultrasounds are used. However, other oscillators having a plane shape can be used.

Figure 3:
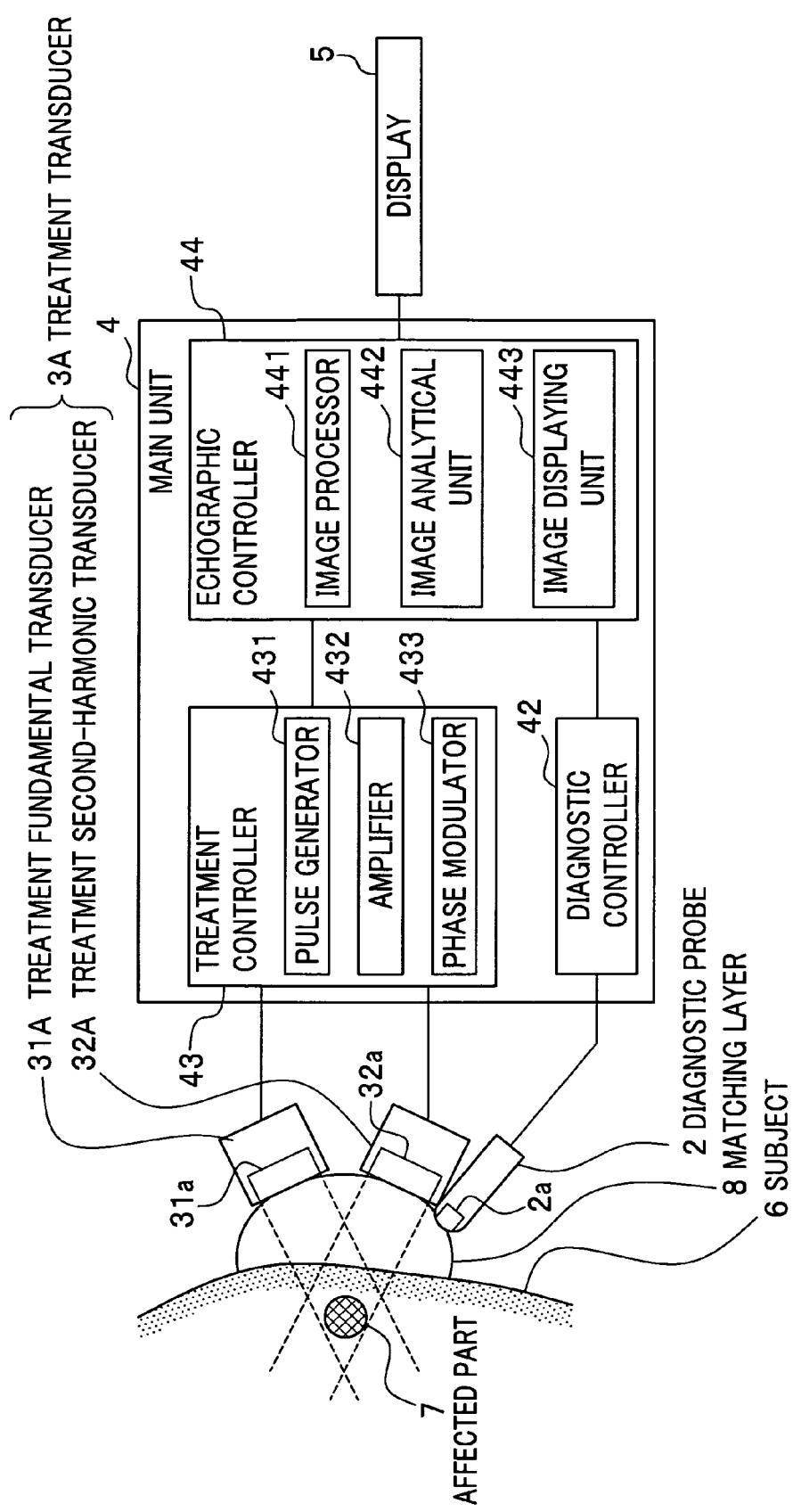
FIG. 3 is a block diagram of a sonodynamic treatment apparatus according to a modification of the present invention.

Will be described with reference to FIG. 3 a modification of the treatment transducer. The same or corresponding elements and parts are designated with the same or corresponding marks used in the embodiment, and thus, their detailed descriptions are omitted. In the modification, as shown in FIG. 3, an oscillator 31a of a treatment fundamental transducer 31A and an oscillator 32a of a treatment second-harmonic transducer 32A are configured in plane. The treatment ultrasound can be radiated toward a broader region with this configuration, an area treated by one operation can be expanded.

EXAMPLES

Hereinafter will be described examples in which the sonodynamic treatment apparatus 1 is used.

Example 1

An example 1 shows a case that the treatment ultrasound is radiated, and then the bubble due to the cavitation is confirmed on the echographic image, followed by treatment ultrasound exposure having the same acoustic intensity.

Figure 4:
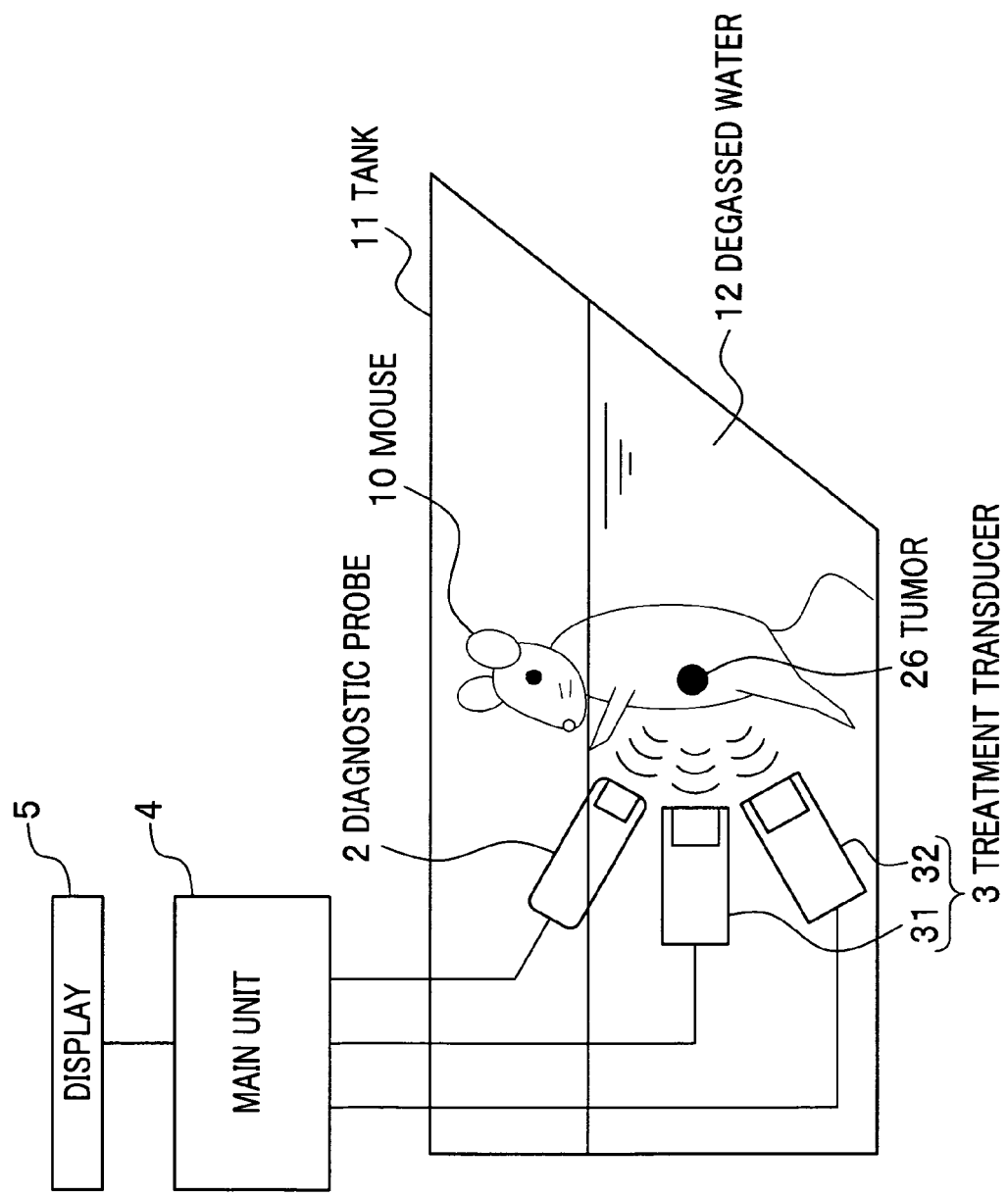
FIG. 4 is an illustration of an experimental system used in an example 1.

FIG. 4 is an illustration of an experimental system using the sonodynamic treatment apparatus 1 in the example 1. As shown in FIG. 4, the sonodynamic treatment apparatus 1 includes the diagnostic probe 2, the treatment fundamental transducer 31, the treatment second-harmonic transducer 32, the main unit 4, and the display 5.

The configuration within the main unit 4 is the same as that described in the embodiment, and thus detailed descriptions are omitted.

As the subject 6, is used a male $CDF_1$ mouse (hereinafter referred to as mouse) 10. Approximately 1 square mm pieces of murine experimental tumor 26 of "colon 26" is initiated subcutaneously into the left femoris of the mouse (five weeks old) 10. When the implanted tumor 26 grows to have a diameter of about 1 cm, it is used in the example 1.

Figure 5:
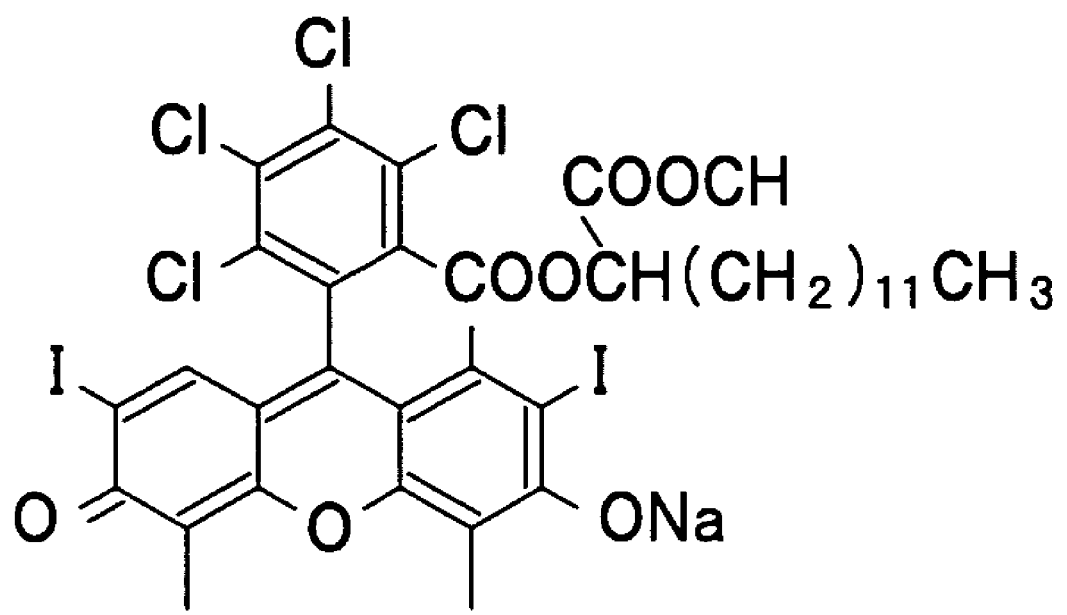
FIG. 5 shows a constitutional formula of tumor-accumulative Rose Bengal derivative used as a sonodynamic sensitizer in the embodiment of the present invention.

FIG. 5 shows a constitutional formula of tumor-accumulative Rose Bengal derivative used as the sonodynamic sensitizer in the above-described embodiment. This medicine of 10 mg/ml PBS solution is administered to mouse 10 by intravenous injection from tail vein. Dose of administered medicine is 30 mg/kg.

When twenty-four hours passed after the medicine is administered, the mouse 10 is anesthetized with Pentobarbital sodium and shaved near the tumor 26. Next, legs are so fixed that the tumor 26 can be located at a window of an acrylic board (not shown.) The acrylic board is fixed to a triaxial stage, and as shown in FIG. 4, the mouse 10 is submerged together with the acrylic board in degassed water 12 in a tank 11. The degassed water is continuously degassed and is maintained to have a temperature of 30° C. Next, the treatment transducer 3 and the diagnostic probe 2 are fixed in the tank 11. Next, the mouse 10 is moved with the triaxial stage so that the tumor 26 of the mouse 10 is located at a focal point 6 cm distant from the treatment transducer 3.

Figure 6:
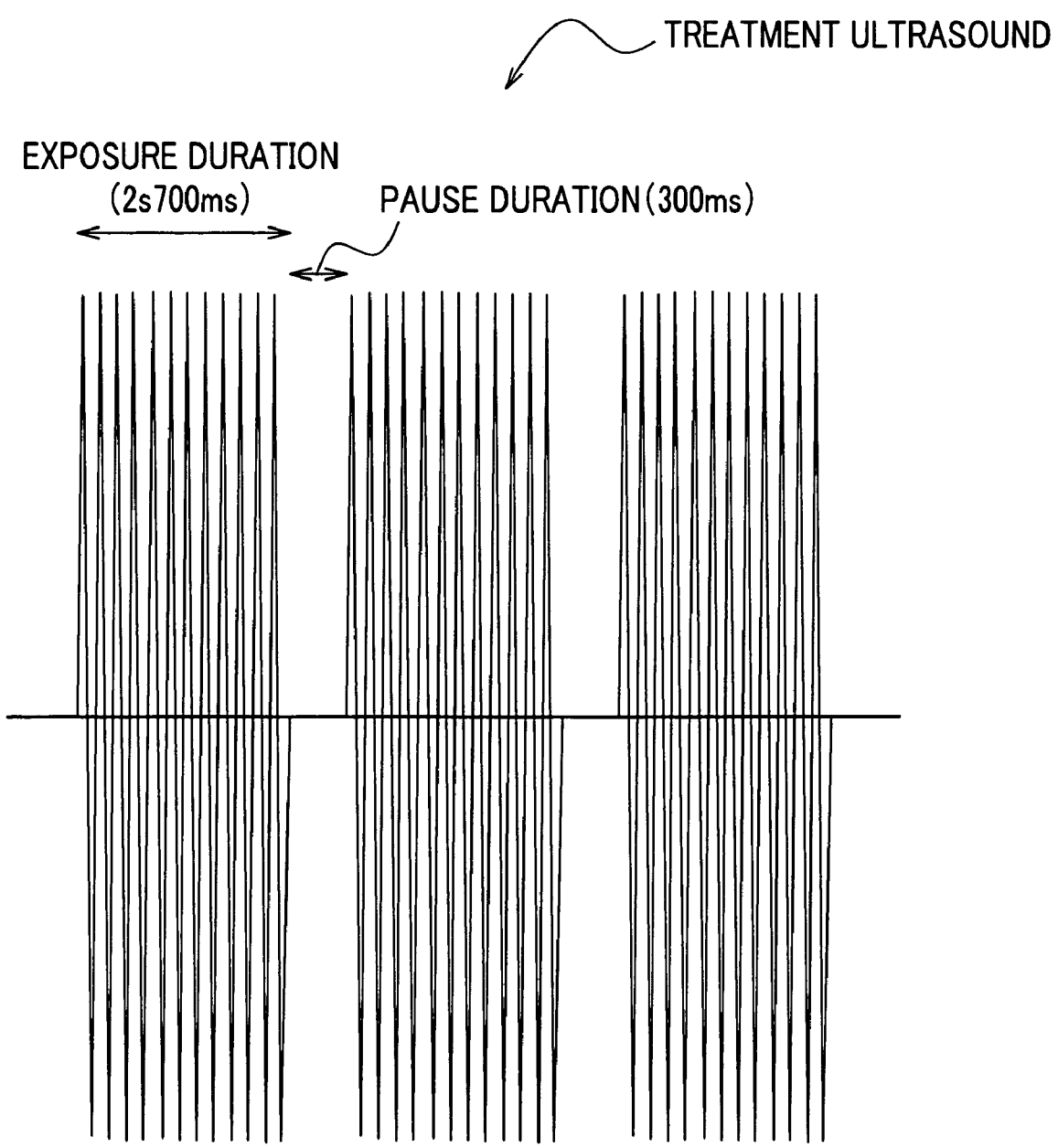
FIG. 6 shows a waveform of the treatment ultrasound radiated by a treatment transducer in the example 1.

FIG. 6 shows a waveform of the treatment ultrasound radiated from the treatment transducer 3 in the example 1. As shown in FIG. 6, the treatment ultrasound is radiated from the treatment transducer 3 with a pulse sequence in which the treatment ultrasound is radiated for 2 s and 700 ms and stopped for 300 ms as a pause duration, and this pattern is repeated. The radiated treatment ultrasounds have a frequency of 0.5 MHz (including 1350 pulses) and a frequency of 1.0 MHz (including 2700 pulses), respectively, and a total acoustic intensity of 200 $W/cm^2$. The ultrasounds radiated by the treatment transducer 3 are synchronized with radiation of the diagnostic ultrasound radiated by the diagnostic probe 2. The treatment ultrasounds are radiated for one minute and the brightness change is observed on the echographic image generated during the pause duration of the pulses of the treatment ultrasounds. In the example 1, the ultrasounds having 0.5 MHz with an acoustic intensity of 0.5 and 1.0 MHz with an acoustic intensity of 0.5, respectively, are superimposed with each other, in other words, superimposed at a ratio of 1:1. However, their intensities may range from 0.1 and 0.9 to 0.9 to 0.1, in other words, the ratio ranges from 1:9 to 9:1.

FIGS. 7A to 7D show echographic images displayed on the display 5 of the example 1. FIG. 7A shows an image in a B-mode used in a general ultrasound diagnostic apparatus for comparison with the imaging method of enhancing the harmonics. The tumor 26 is displayed on there. FIGS. 7B to 7D show echographic images generated by a method of enhancing the harmonics, wherein the signals from the tumor 26 including much fundamental component are almost cancelled, so that the tumor 26 is invisible. Among the echographic images generated by the method of enhancing the harmonics, FIG. 7B shows an image before the treatment ultrasound exposure, FIG. 7C shows an image during treatment ultrasound exposure, and FIG. 7D shows an image after treatment ultrasound exposure. The echographic image of treatment shows in FIG. 7C during ultrasound exposure, wherein the brightness change corresponding to the bubble cannot be observed, because inference is occurred between the treatment ultrasound and the diagnostic ultrasound. However, the echographic image after the ultrasound exposure shows in FIG. 7D the brightness change at the focal point 27 of the treatment ultrasound. The mouse 10 is euthanized two days after ultrasound exposure to remove the tumor 26 and then it is fixed with formalin. After this, a murine tumor-tissue section is prepared to actually observe the tumor 26 to judge the treatment effect. FIG. 8A shows a tumor-tissue section before staining and FIG. 8B shows a tumor-tissue section after HE (Hematoxylin-Eosin) staining. As shown in FIG. 8A, at the murine tumor-tissue section before staining, a necrosis region 28 is clearly observed. In addition, as shown in FIG. 8B, at the murine tumor-tissue section HE stained, the necrosis region 28 is thinner than other portions in staining, which is inherent to the Hematocylin, showing occurrence of some damage such as disappearance of nucleus and pyknosis.

FIG. 9 illustrates a table showing a correlation between a group observed the brightness change on the echographic image during the treatment and a group observed a treatment effect on the murine tumor-tissue sections. As shown in FIG. 9, when the brightness change was observed on the echographic image (with observation), in all of three samples were observed the necrosis regions 28 with treatment effect. On the other hand, when the brightness change was not observed on the echographic image (without observation), among three samples two samples did not show the treatment effect in the tumor-tissue sections. However, in one example the necrosis region 28 was observed for the treatment effect. Even in the case that the brightness change was not observed, there may be the treatment effect. However, the result demonstrates that the case with the brightness change surely shows the treatment effect.

In other words, it is demonstrated that there is clearly the correlation between the group with the observation of the brightness change during the treatment using the sonodynamic treatment apparatus 1 and the group with the observation of the treatment effect by actually observing the tumor-tissue sections after several days.

In addition, in a case that the ultrasound obtained by superimposing an ultrasound having a frequency of 0.5 MHz onto an ultrasound having a frequency of 1.0 MHz with a low total acoustic intensity around 60 $W/cm^2$ is radiated for two minutes, there is no observation of the brightness change during the treatment.

Example 2

In an example 2, the treatment ultrasound pulses are radiated, and after the bubble is detected on the echographic image, the acoustic intensity of the treatment ultrasound pulses is decreased.

Figure 10:
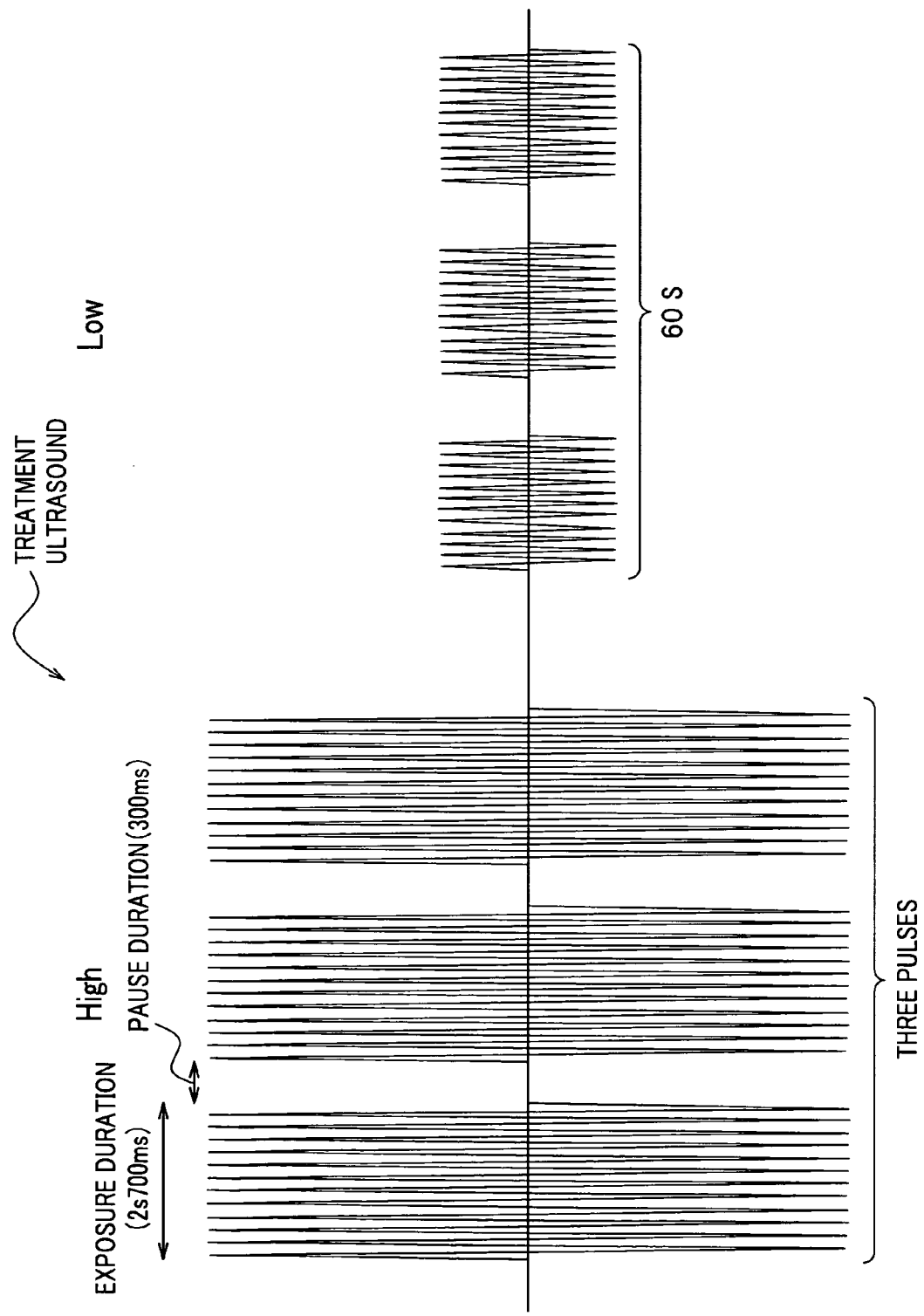
FIG. 10 shows a waveform of the treatment ultrasound radiated from the treatment transducer 3 in an example 2.

FIG. 10 shows a waveform of the treatment ultrasound radiated from the treatment transducer 3 in the example 2. As shown in FIG. 10, the treatment ultrasound is radiated from the treatment transducer 3 with a pulse sequence in which the treatment ultrasound is radiated to have an exposure duration of 2 s 700 ms and then radiation is interrupted for 300 ms. The frequencies of the radiated treatment ultrasounds are 0.5 MHz (including 1350 pulses) and 1.0 MHz (including 2700 pulses). In the example 2, as shown in FIG. 10, first the first ultrasound (designated with HIGH) with a high total acoustic intensity of 200 W/cm$^2$ to have three pulses, and then a second ultrasound (designated with LOW in FIG. 10) is radiated for one minute with a total of 60 W/cm$^2$. In the example 2, the ultrasounds having 0.5 MHz with an intensity of 0.5 and 1.0 MHz with an intensity of 0.5, respectively, are superimposed, in other words, superimposed at a ratio of 1:1. However, their intensities may range from 0.1 and 0.9 to 0.9 to 0.1, in other words, the ratio ranges from 1:9 to 9:1.

The brightness change on the echographic image generated for the pause duration of the treatment ultrasound pulses is observed on the display 5. The mouse 10 is euthanized after the ultrasound exposure to remove the tumor 26, and then it is fixed with formalin. After this, a murine tumor-tissue section is prepared to actually observe the tumor 26 to judge the treatment effect.

FIG. 11 illustrates a table showing a correlation between a group observed the brightness change on the echographic image during the treatment and a group observed a treatment effect on the murine tumor-tissue sections.

In a case that the brightness change is continuously observed on the echographic image during radiation of the first and second ultrasounds (with brightness change), in all five examples, the necrosis regions 28 were observed with the treatment effect.

On the other hand, in a case that the brightness change was not observed or became not observed during the exposure (without the brightness change), among three samples two samples did not show the treatment effect in the tumor-tissue sections. However, in one example the necrosis region 28 was observed for the treatment effect. Even in the case that the brightness change was not observed, there may be the treatment effect. However, the result demonstrates that the case with the brightness change surely shows the treatment effect.

Results of the example 1 and the example 2 showed that when the acoustic intensity is set to 200 W/cm$^2$ and the brightness change is observed on the echographic image, all samples showed the treatment effect. Further, once the bubble was detected, if the acoustic intensity of the treatment ultrasound was decreased, as far as the brightness change was appropriately observed on the echographic image, the treatment effect was observed through the observation of the tumor-tissue section.

The examples 1 and 2 demonstrate that the sonodynamic treatment is surely performed by making the brightness change on the echographic image during the treatment an index.

As mentioned above, according to the present invention, tumors or the like can be treated with monitoring generation of the bubble effective to the sonodynamic treatment, caused by the cavitation.

The invention claimed is:

1. A sonodynamic treatment apparatus comprising:
a first ultrasound radiating unit for radiating a diagnostic ultrasound;
a second ultrasound radiating unit for radiating a treatment ultrasound;
an echo detection unit for detecting an ultrasound echo corresponding the diagnostic ultrasound;
a diagnostic controller for radiating the diagnostic ultrasound with the first ultrasound radiating unit and detecting the ultrasound echo;
an echographic controller for processing an echographic image on the basis of the detected ultrasound echo;
a treatment controller for radiating the treatment ultrasound with the second ultrasound radiating unit; and
an echographic analyzer for detecting a bubble generated on the echographic image in response to radiation of the treatment ultrasound,
wherein the treatment controller comprises a pulse generator for controlling radiation of the treatment ultrasound with the second ultrasound radiating unit to have a predetermined exposure duration and a predetermined pause duration of the treatment ultrasound, and an amplifier that decreases an acoustic intensity of the treatment ultrasound radiated by the second ultrasound radiating unit when the bubble is detected and increases the acoustic intensity of the treatment ultrasound radiated by the second ultrasound radiating unit when the bubble is not detected, and
wherein the echographic controller processes the echographic image on the basis of the ultrasound echo during the pause duration of the treatment ultrasound.

2. The sonodynamic treatment apparatus as claimed in claim 1, wherein the treatment controller controls the exposure duration and the pause duration within ranges in which growth of the bubble in a subject is maintained.

3. The sonodynamic treatment apparatus as claimed in claim 2, wherein the echographic controller generator generates the echographic image in brightness, the sonodynamic treatment apparatus further comprising:
an image analytical unit that detects a brightness change on the echographic image, wherein the treatment controller determines the exposure duration and the pause duration in accordance with a brightness change on the echographic image.

4. The sonodynamic treatment apparatus as claimed in claim 1, wherein the treatment controller generates a first ultrasound to have three or more pulses of the treatment ultrasound and the pause duration equal to or less than 500 ms.

5. The sonodynamic treatment apparatus as claimed in claim 1, wherein the treatment controller generates a first ultrasound having a first acoustic intensity enough to nucleate the bubble in a subject and after this, generates a second ultrasound having a second acoustic intensity lower than the first acoustic intensity enough to maintain growth of the bubble.

6. The sonodynamic treatment apparatus as claimed in claim 5, further comprising an image analytical unit that detects a brightness change on the echographic image to detect the bubble on the echographic image, wherein the first acoustic intensity is progressively increased until the bubble is detected.

7. The sonodynamic treatment apparatus as claimed in claim 1, wherein the second ultrasound radiating unit radiates the treatment ultrasound using a fundamental wave and a second harmonic wave so as to perform superimposing the fundamental wave onto the second harmonic wave at an affected part.

8. The sonodynamic treatment apparatus as claimed in claim 1, wherein the pulse generator generates an ultrasound signal including a fundamental wave and a second harmonic wave; and further comprising a phase modulating unit that phase-shifts the second harmonic wave from the fundamental wave to have a phase interval equal to or greater than 10 ms, the fundamental wave and the phase-shifted second harmonic wave being radiated from the second ultrasound radiating unit.

9. The sonodynamic treatment apparatus as claimed in claim 1, wherein the second ultrasound radiation unit comprises focusing oscillators that focus the treatment ultrasound to generate a focused ultrasound.

10. The sonodynamic treatment apparatus as claimed in claim 9, wherein the second ultrasound radiation unit comprises a variable focusing unit for changing a focal point of the focused ultrasound.

11. The sonodynamic treatment apparatus as claimed in claim 1, wherein the diagnostic controller stops radiating the diagnostic ultrasound while the treatment ultrasound is radiated.

12. The sonodynamic treatment apparatus as claimed in claim 1, wherein the echographic controller generates the echographic image on the basis of harmonics included in the detected ultrasound echo.

13. The sonodynamic treatment apparatus as claimed in claim 12, wherein the diagnostic image processor generates the echographic image on the basis of harmonic waves included in the detected ultrasound echo, the harmonic waves having frequencies of n times a fundamental frequency of the detected echo and subharmonic waves, n being given a natural number.

14. The sonodynamic treatment apparatus as claimed in claim 1, wherein the echographic controller generates the echographic image in brightness, the sonodynamic treatment apparatus further comprising:
  an image analytical unit that detects a brightness change on the diagnostic image;
  and
  a frequency controller that progressively increases a frequency of an ultrasound signal generated by the pulse generator up to 4.5 MHz when the image analytical unit does not detect the brightness change.

15. The sonodynamic treatment apparatus as claimed in claim 1, wherein the first ultrasound radiating unit radiates the diagnostic ultrasound to have a first exposure duration, the second ultrasound radiating unit radiates the treatment ultrasound to have a second exposure duration greater than the first exposure duration.

* * * * *